United States Patent [19]

Shimizu et al.

[11] Patent Number: 4,596,156
[45] Date of Patent: Jun. 24, 1986

[54] SAMPLE GAS EXTRACTING APPARATUS

[75] Inventors: Sumio Shimizu; Hiroji Kohsaka, both of Kyoto, Japan

[73] Assignee: Horiba, Ltd., Kyoto, Japan

[21] Appl. No.: 580,632

[22] Filed: Feb. 16, 1984

[30] Foreign Application Priority Data

Jun. 4, 1983 [JP] Japan ............................... 58-101556

[51] Int. Cl.⁴ .............................................. G01N 1/26
[52] U.S. Cl. ............................... 73/863.31; 73/863.61; 137/599.1; 137/607
[58] Field of Search .................. 73/28, 863.58, 863.61, 73/864.34, 863.31; 137/599, 599.1, 607

[56] References Cited

U.S. PATENT DOCUMENTS 3,527,245  9/1970  Lamontagne .................... 137/599.1
3,699,814 10/1972  Kaufman ......................... 73/864.34
3,824,770  7/1974  Eckstein ........................... 137/599.1
3,830,256  8/1974  Cox .................................... 137/599
3,896,673  7/1975  Audouze et al. ............... 73/864.34
3,905,394  9/1975  Jerde ................................ 137/599
4,030,523  6/1977  Cram et al. ..................... 137/599

Primary Examiner—David L. Lacey
Attorney, Agent, or Firm—Wenderoth, Lind & Ponack

[57] ABSTRACT

A sample gas extracting apparatus constituted by a plurality of parallel connected constant flow-rate gas lines each having a critical flow Venturi connected in the downstream portion, relative to the direction of gas flow therethrough, thereof and a changeover valve in the upstream portion, relative to the direction of gas flow therethrough, thereof which can be changed over for passing sample gas to the corresponding critical flow Venturi or for passing air to the corresponding critical flow Venturi. A sample gas line is connected to the upstream end of the parallel connected constant flow-rate gas lines and has a sample gas extracting device connected therein just upstream of the constant flow-rate gas lines. A suction device is connected to the downstream end of the parallel connected constant flow-rate gas lines and having a suction capacity greater than the total of the critical gas flow rates of the critical flow Venturi's and less than that which will cause a surging phenomenon in the apparatus.

4 Claims, 4 Drawing Figures

SAMPLE GAS EXTRACTING APPARATUS

BACKGROUND OF THE INVENTION

1. Field of the Invention

The present invention relates to an improved sample gas extracting apparatus for use in the analysis of ingredients contained in an exhaust gas discharged from, for example, an internal combustion engine or the like.

2. Prior Art

A representative conventional sample gas extracting apparatus is shown in FIG. 1. This apparatus consists of a sample gas line 21, which carries a mixture of an exhaust gas and a diluent gas, e.g. air, in the direction of the arrow and provided with a Critical Flow Venturi (CFV)20; a suction apparatus 22 for maintaining the pressure difference between the upstream and downstream ends, relative to the directions of the flow of the gas, of said CFV 20 at a value higher than the critical differential pressure in said CFV 20, and a sample gas extracting line 23 for extracting a quantity of the sample gas supplied to the upstream end of said CFV 20 from said sample gas line 21. At this time, since the critical gas flow rate $Q_1$ of said CFV 20 and the quantity Q of the sample gas in said sample gas line 21 are known, the sample gas can be extracted into said sample gas extracting line 23 at a ratio corresponding to the ratio of $Q/Q_1$.

Said CFV 20 is replacable by previously prepared CFV's 20', 20" ... having different critical gas flow rates $Q_1$.

However, this conventional apparatus has the follow defects:

Although said suction apparatus 22, which has a sufficient suction force for holding said CFV 20 at the critical differential pressure when said sample gas line 21 has a CFV 20 with the largest critical gas flow rate $Q_1$ therein, when such CFV 20 is replaced by one having a smaller critical gas flow rate $Q_1$, a surging phenomenon is produced in said suction apparatus 22 at a critical gas flow rate $Q_1$ at which about ⅓ the suction apparatus is performing at the suction capacity. This makes necessary the addition of a surge preventing apparatus 27 consisting of a throttle valve 24, a stop valve 25 and an air filter 26 or the like through which supplemental air is supplied into line 21 downstream of CFV 20. Said surge preventing apparatus 27 must be larger than the suction capacity of said suction apparatus 22. The surge preventing apparatus 27 thus makes necessary a larger size installation space for the overall apparatus.

In addition, there has been a problem during operation since said CFV 20 must be replaced every time the extracting ratio of sample gas, that is to say the flow rate in said sample gas line 21 is changed.

OBJECT AND BRIEF SUMMARY OF THE INVENTION

It is, therefore, an object of the present invention to provide an improved sample gas extracting apparatus capable of very easily carrying out a change in the flow rate in the sample gas line and preventing a surging phenomenon from being produced regardless of how the flow rate is changed, but without requiring a larger sized surge preventing apparatus such as has conventionally been required.

This object is achieved by the provision of a sample gas extracting apparatus, comprising: a plurality of parallel connected flow-rate gas lines each having a critical flow Venturi connected in the downstram portion thereof, and a changeover valve in the upstream portion thereof which can be changed over for passing sample gas to the corresponding critical flow Venturi or for passing air to the corresponding critical flow Venturi; a sample gas line connected to the upstream end of said parallel connected constant flow-rate gas lines and having a sample gas extracting means connected therein just upstream of said constant flow-rate gas lines; and a suction means connected to the downstream end of said parallel connected constant flow-rate gas lines and having a suction capacity greater than the total of the critical gas flow rates of the critical flow Venturis and less than that which will cause a surging phenomenon in said apparatus.

BRIEF DESCRIPTION OF THE DRAWINGS

The invention will now be described in greater detail in connection with the accompanying drawings, in which.

DESCRIPTION OF THE PREFERRED EMBODIMENT

Figure 1:
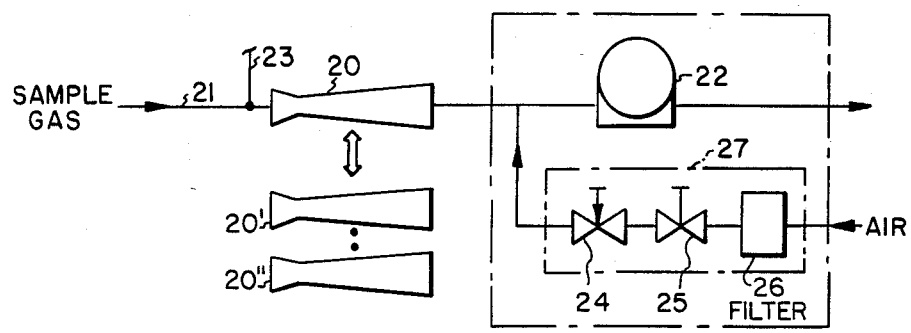
FIG. 1 is a schematic diagram showing a conventional sample gas extracting apparatus.
Figure 2:
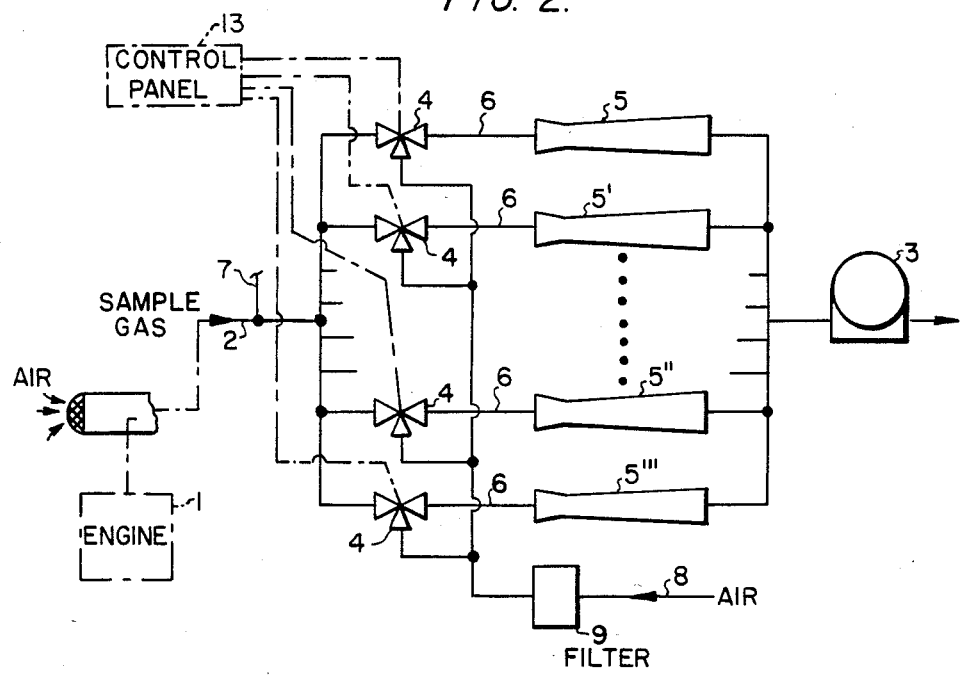
FIG. 2 is a diagram similar to FIG. 1 of the constant-volume sample gas extracting apparatus according to the present invention.

The sample gas extracting apparatus shown in FIG. 2 comprises a plurality of the constant-flow rate lines 6 connected in parallel to each other and having respective upstream ends connected to a downstream end of a single sample gas line 2 which has an upstream end adapted to be connected to an internal combustion engine to receive a mixture of an exhaust gas discharged in the direction of the arrow from the internal combustion engine 1 or some other source of gas to be sampled, and having downstream ends connected to a suction apparatus 3 such as a blower. Each line 6 has a three-way changeover valve 4 installed in the upstream portion, relative to the direction of flow of the gas therethrough, thereof and a CFV's 5, 5',5", 5''' ... installed in the downstream portion, relative to the direction of flow of the gas therethrough, thereof. A sample gas extracting line 7 for extracting a quantity of the sample gas is connected with said sample gas line 2 between the upstream and downstream ends thereof.

Each of said changeover valves 4 has a branch from an air supply line 8 connected thereto and can be selectively changed over from a state in which only sample gas is introduced into the corresponding CFV from said sample gas line 2, to a state in which only the air is introduced into the corresponding CFV from the air supply line 8.

Said CFV's 5, 5', 5", 5''' ... each have a different critical gas flow rate. Said suction apparatus 3 has a suction capacity larger than the total of the critical flow rates of all of said CFV's 5, 5',5", 5''' ... together, but no so much greater as to produce a surging phenomenon, that is to say, the suction capacity is such that all of said CFV's are held at the critical differential pressure but no surging phenomenon being produced. The total of the gas flow rates of the CFV's should be greater than ⅓ the suction capacity of the suction apparatus to avoid surging. An air filter 9 is provided in air supply line 8.

Figure 3A:
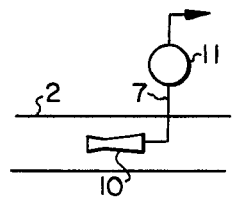
FIGS. 3a and 3b are schematic views showing preferred embodiments of a sample gas extracting means for use with the apparatus of FIG. 2.
Figure 3B:
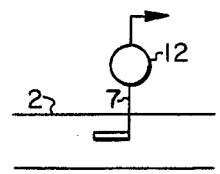

The sample gas extracting means shown in FIG. 3a has a CFV 10 installed in said sample gas line 2, the sample gas extracting line 7 connecting said CFV 10 to a suction apparatus 11 for holding said CFV 10 at the critical differential pressure. The sample gas extracting means shown in FIG. 3b has said sample gas extracting line 7 open in the upstream direction in said sample gas line 2, said sample gas extracting line 7 being connected to a suction apparatus 12 of the constant-volume type, or a similar type of suction apparatus.

Further, a control panel 13 with lines connected to the changeover valves 4 is provided for the remote control of said changeover valves 4.

With the above described construction, the quantity of the sample gas extracted can be changed in a remarkable multistage fashion without producing any surging phenomenon. The suction of said pump 3 is always constant, because changing-over of said changeover valve 4 in said constant-flow rate lines 6 merely causes air from air supply line 8 to be substituted for the sample gas, or vice versa. There can be N flow rates produced by various permutations and combinations of N CFV's, all of which have different critical flow rates. The flow rate can be very easily changed merely by selectively changing-over said changeover valves 4 whithout the necessity of the conventional troublesome operation of exchanging CFV's. In addition, no surging phenomenon is produced because the total of the critical gas flow rates of all the CFV's is larger than ⅓ the suction capacity of said suction apparatus 3. The sum of the critical gas flow rates of all CFV's and the suction capacity of said suction apparatus 3 are always constant regardless of how the quantity of the sample gas is changed, because even if the quantity of the sample gas is reduced to a value less than ⅓ times the suction capacity of said suction apparatus 3, the valves 4 can be set to admit air to the CFV's not needed for exhaust gas.

In addition although CFV's 5,5',5",5"' . . . which are used in the above described preferred embodiment, all have different critical gas flow rates, it is possible for only a part of the plurality to have different critical flow rates, or all of them may have the same critical gas flow rate.

Further, two two-way valves may be used instead of a three-way valve for each said changeover valve 4. Also manually operatable valves can be used.

As described above, the sample gas extracting apparatus according to the present invention has a plurality of the constant-flow rate lines in each of which is a CFV, respectively, in the downstream portion thereof and a changeover valve in the upstream portion thereof which can be selectively changed-over to pass only the sample gas or to pass only air, said constant-flow rate lines being arranged in parallel between a sample gas line and a suction apparatus, and a sample gas extracting line being connected to said sample gas line.

According to the above described construction, not only can the flow rate of the sample gas be changed by a very easy operation of selectively changing-over changeover valves without requiring the conventional troublesome operation of exchanging CFV's, but also no surging phenomenon is produced at all regardless of how the flow rate is changed, since the ratio of the suction capacity of the suction apparatus to the sum total of the suction flow rates of the CFV's is constant. Consequently, no separate apparatus for preventing surging from being produced is required.

In addition, the flow rate can be changed to a remarkable number of different flow rates by using CFV's having the same or different critical suction flow rates in spite of the small number of CFV's.

What is claimed is:

1. A sample gas extracting apparatus, comprising:
a plurality of parallel connected constant flow-rate gas lines each having an upstream end and a downstream end and a critical flow Venturi connected therein adjacent the downstream end thereof and a changeover valve connected therein adjacent the upstream end thereof said valves being constructed so as to be changed over for passing sample gas from the upstream end to the corresponding critical flow Venturi or for passing air to the corresponding critical flow Venturi;
a sample gas line connected to the upstream end of said parallel connected constant flow-rate gas lines for supplying sample gas thereinto and having a sample gas extracting means connected therein just upstream of said constant flow-rate gas lines;
an air supply means and air supply lines connected between said air supply means and said changeover valves; and
a suction means connected to the downstream end of said parallel connected constant flow-rate gas lines and having a suction capacity greater than the total of the critical gas flow-rates of the critical flow Venturis and less than that which will cause a surging phenomenon in said apparatus.

2. A sample gas extracting apparatus as claimed in claim 1 in which said changeover valves are three-way valves.

3. A sample gas extracting apparatus as claimed in claim 2 further comprising means connected to said three-way valves for controlling said valves remotely.

4. A sample gas extracting apparatus as claimed in claim 2 in which at least some of said Venturis having a critical flow rate different from the critical flow rate of the others.

* * * * *